(12) United States Patent
Hameed et al.

(10) Patent No.: US 9,643,169 B1
(45) Date of Patent: May 9, 2017

(54) PROCESS FOR THE PREPARATION OF QUINOLINE BASED IONIC FLUORIDE SALTS (QUFS)

(71) Applicants: Abdul Hameed, Karachi (PK); Nafees Iqbal, Karachi (PK); Jamshed Hashim, Karachi (PK); Khalid Mohammed Khan, Karachi (PK); Syed Tarique Moin, Karachi (PK); Shakeel Ahmad, Karachi (PK); Syed Abid Ali, Karachi (PK); Fatima Zahra Basha, Karachi (PK); Mariya al-Rashida, Lahore (PK); Rima D. Alharthy, Jeddah (SA); Shahnaz Perveen, Karachi (PK)

(72) Inventors: Abdul Hameed, Karachi (PK); Nafees Iqbal, Karachi (PK); Jamshed Hashim, Karachi (PK); Khalid Mohammed Khan, Karachi (PK); Syed Tarique Moin, Karachi (PK); Shakeel Ahmad, Karachi (PK); Syed Abid Ali, Karachi (PK); Fatima Zahra Basha, Karachi (PK); Mariya al-Rashida, Lahore (PK); Rima D. Alharthy, Jeddah (SA); Shahnaz Perveen, Karachi (PK)

( * ) Notice: Subject to any disclaimer, the term of this patent is extended or adjusted under 35 U.S.C. 154(b) by 0 days.

(21) Appl. No.: 15/158,867

(22) Filed: May 19, 2016

(51) Int. Cl.
*C07D 215/10* (2006.01)
*B01J 31/02* (2006.01)

(52) U.S. Cl.
CPC ........ *B01J 31/0298* (2013.01); *C07D 215/10* (2013.01); *B01J 2231/341* (2013.01); *B01J 2531/002* (2013.01)

(58) Field of Classification Search
CPC .................................................... C07D 215/10
USPC ......................................................... 546/182
See application file for complete search history.

(56) References Cited

PUBLICATIONS

Iqbal et al., "Solvent-free, etc.," RSC Adv., 2015, 5, 95061-95072.*

* cited by examiner

*Primary Examiner* — Patricia L Morris
(74) *Attorney, Agent, or Firm* — Sarfaraz K. Niazi

(57) ABSTRACT

The current invention relates to ionic liquid preparation and their application in organic synthesis. More specifically, the present invention relates to the quinoline based ionic liquids having fluoride counter anion and their applications in click chemistry, Knoevenagel condensation to 1,2,5,6-tetrahydronicotinonitrile (12), and pyrazol (15) formation.

3 Claims, 11 Drawing Sheets

PROCESS FOR THE PREPARATION OF QUINOLINE BASED IONIC FLUORIDE SALTS (QUFS)

FIELD OF INVENTION

The present invention relates to the preparation of quinoline based ionic liquids having fluoride counter anion (QuFs) to use as catalysts in organic reaction which include click chemistry, Knoevenagel condensation and pyrazole formation.

BACKGROUND OF INVENTION

Ionic liquids (ILs) have been used in lieu of traditional solvents in organic synthesis due to their unique physiochemical properties such as low volatility, significant thermal stability, and ease of recovery. ILs offer clean solvent-free environment to carry out a variety of eco-friendly reactions.

Imidazole or pyridine-based ionic liquids with varied range of counter anions have commonly been used as catalysts in synthetic chemistry. However, the inert nature of imidazole and well-known toxicity of pyridine is an impediment towards further expanding the scope of ionic liquids. Herein, we have employed non-toxic quinoline as a head group for the synthesis of N-alkylated ionic liquids.

Quinoline is an important scaffold in a number of compounds of medicinal and pharmaceutical interest. Quinoline-based ionic salts have not yet been explored as catalysts in organic synthesis. Quinoline-based ionic liquids can be easily prepared via a simple alkylation and subsequent counter-ion exchange under conventional environment, without employing any strict controlled reaction conditions. In this study, the counter anions (i.e. $I^-$, $Br^-$) of the corresponding ionic salts were exchanged with fluoride ions ($F^-$), which is known to act as a mild base in various organic reactions.

The quinoline-based ionic liquids with fluoride counter anion have a close resemblance with tetrabutyl ammonium fluoride (TBAF), a well-known catalyst in organic reactions. In order to explore the catalytic potential of synthesized QuFs, click reaction, and other multicomponent reactions were carried out under solvent-free conditions.

Click chemistry was used for the synthesis of 5-(p-methylphenyl)-1H-tetrazole (7). Keeping in view the hygroscopic nature of ionic liquids, the effect of successively increasing concentration of water on synthetic output of the reaction employing QuF (4) as ionic liquid was investigated in detail (FIG. 1).

Tetrazole serves as an isosteric substituent for carboxylic acid group in many compounds of pharmaceutical interest. The tetrazole moiety improves the metabolic resistance and also the pharmacokinetic properties of drugs. Multicomponent reactions carry unique place in synthesis and medicinal chemistry to build different compounds libraries for biological screening purposes.

A wide range of applications of ionic liquids have been reported owing to a number of unique physical properties including thermodynamic and ion transport properties. These properties of ionic liquids vary widely depending on the nature of the cation and anion, therefore, such properties should ideally be known prior to the use of an ionic liquid.

Transport properties of ions are of great significance that need to be estimated for the design of new ionic liquids for use as electrolytes or in electrochemical devices. Different properties of ionic liquids can be assessed by means of experimental techniques and can also be simulated by means of molecular dynamics (MD) simulation. Hence structural and dynamic properties of QuF derivatives in bulk, including self-diffusion coefficients were investigated by employing molecular dynamics simulations.

Density functional theory (DFT) calculations were used to gain structural insight into QuF ionic liquids. The stability of such ionic liquids is of paramount interest, hence binding energy calculations were performed in comparison to tetrabutyl ammonium fluoride (TBAF), a commercially available ionic liquid.

BRIEF SUMMARY OF THE INVENTION

The current invention relates to ionic liquid preparation and their application in organic synthesis.

More specifically, the present invention relates to the quinolone based ionic liquids having fluoride counter anion and their applications in click chemistry, Knoevenagel condensation to 1,2,5,6-tetrahydronicotinonitrile (12), and pyrazol (15) formation.

In an embodiment, the present invention demonstrates the preparation of quinolone based ionic liquids (QuFs) via two steps 1) N-alkylation and counter anions ($Br^-$ or $I^-$) exchange with fluoride ($F^-$). The quinolone based ionic liquids has been used as catalysts and solvent to preform i) click reaction of 1H-tetrazole (5) formation, ii) Knoevenagel condensation and dimerization to afford 1,2,5,6-tetrahydronicotinonitrile (12), and iii) pyrazole formation. Thermal stability as well as computational studies of QuFs has also been carried out in the present invention.

DETAILED DESCRIPTION OF THE INVENTION

Figure 1:
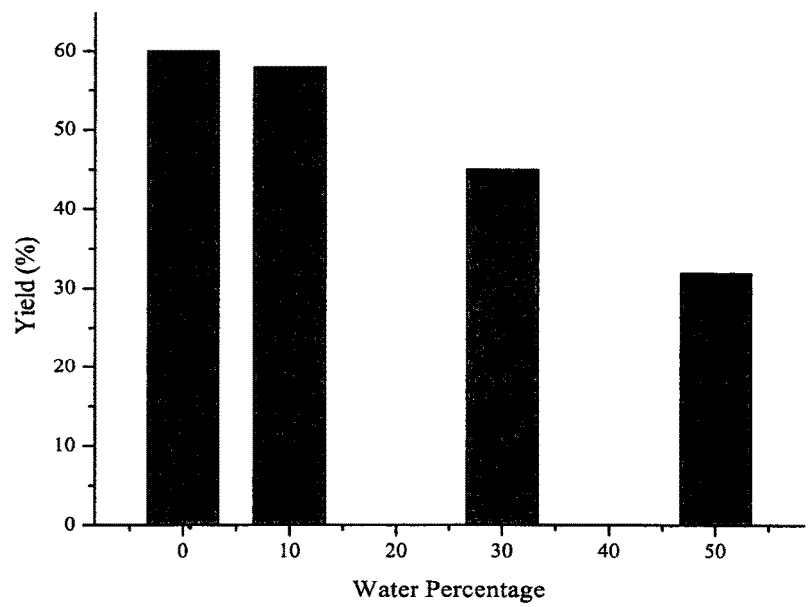
FIG. 1 depicts water effects on reaction output; 1H-tetrazole (7); Reaction conditions: 4'-methyl benzonitrile (1 mmol), $TMSN_3$ (2 mmol), QuF-$C_5$ (4) (1 mmol), MW 120° C., 2 h, Quenched with aqueous 1M HCl.

A synthetic layout of quinoline-based ionic liquids (QuFs) (3-5) is given in Scheme-1. The synthetic scheme involved two steps; 1) N-alkylation of quinoline (1) with alkyl halides, and 2) fluoride ion exchange to obtain the desired ionic salts in 80-95% yield. The N-alkylation of quinoline (1) was carried out using alkyl halides of different chain lengths ($C_2$, $C_5$, and $C_7$). Attachment of longer alkyl chains have been known to affect the catalytic efficiency of ionic liquids due to their steric hindrance.[25]

Alkylation with alkyl iodides ($C_2$) was found to occur in less time as compared to alkyl bromides ($C_5$ and $C_7$) this is attributed to group leaving characteristics of halides. Next the counter ion (either I⁻ or Br⁻) of the resultant ionic liquid was exchanged with fluoride ion (F⁻). Potassium fluoride was used as fluoride ion source in the mixture of water/methanol (1:1) at room temperature. The structures of the desired QuFs (3-5) were confirmed via different spectroscopic techniques including ¹H and C NMR, IR, and mass spectroscopy (Er and HRMS). Reactions have also been scaled up to 3-5 g (23-39 mmol) to validate the synthetic layout.

Scheme-1 Synthesis of quinoline-based ionic fluoride salts.

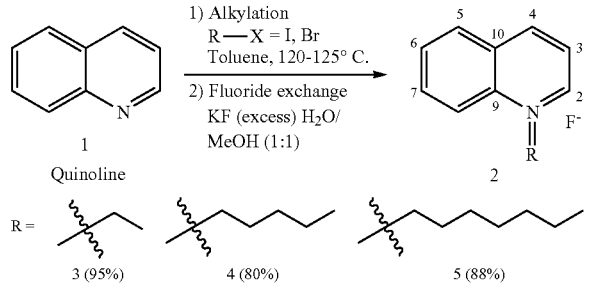

Applications of quinoline-based fluoride ionic liquids (QuFs) as catalyst in organic synthesis, under solvent-free conditions, were explored by preforming different reactions. Initially, click chemistry for tetrazole formation was explored. 1H-tetrazole (7) was constructed from benzonitrile (6), as substrate, on coupling with an azide source (TMSN₃) in the presence of neat QuFs (3-5). TMSN₃ is used as azide source for [3+2]-cycloaddition with nitrile (CN) group to form tetrazole ring.

Fluoride ion has much affinity for silicon atom to release active azide species. In some previous methods, neat TBAF or 1,8-diazabicycloundec-7-ene (DBU)-based ionic liquids with fluoride counter anion has been used for click reaction for tetrazole synthesis. In the present invention, we used new quinoline-based fluoride salts to catalyze click reaction. Although, quinoline scaffold is a part of many pharmaceutical products of interest, the use of quinoline, or its modified forms, in organic synthesis as catalyst is not well explored. The quinoline-based fluoride salts (3-5) are easy to prepare and can serve as mild reagents to catalyze organic reactions. Typically, click reaction for tetrazole formation was performed using neat quinoline-based fluoride salts as under solvent-free conditions. Both conventional heating and microwave irradiation was employed for the reaction. QuF (3) gave desired tetrazole in only trace amount or low yield (18% using microwave irradiations) under solvent-free conditions which may be due to insufficient diffusion of reactants in QuF (3) medium as it exists in solid form. While, the click reaction with QuFs (4) or (5) occurred smoothly to yield 1H-tetrazole (7) in 54-60% yield. As expected, the reaction time observed under microwave irradiation was less than conventional heating (Table-1).

Scheme-2: Solvent-free 1H-tetrazole (7) formation in quinoline fluoride salts

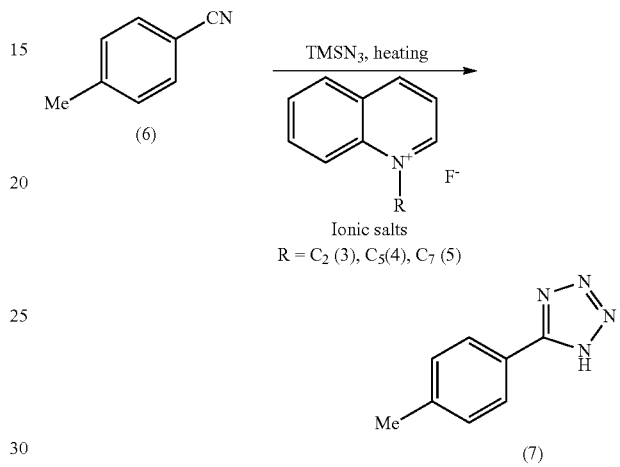

TABLE 1

Tetrazole synthesis under conventional heating and microwave irradiations

| Ionic salts | Reaction Time (h) | | Yield (%) | |
| --- | --- | --- | --- | --- |
| (QuFs) | Δ[a] | MW[b] | Δ | MW |
| 3 | 6.0 | 2.5 | traces | 18 |
| 4 | 5.5 | 2.5 | 54 | 60* |
| 5 | 6.0 | 2.5 | 41 | 55 |

[a] = conventional heating (100-105° C.);
[b] = microwave irradiation (140° C.)
*Scaled up reaction up to 2 mmol with 4'-methylbenzonitrile

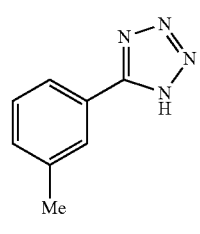

(7b)

65%

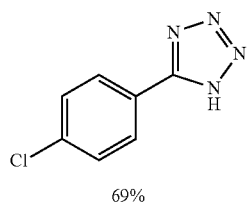

(7c)

69%

-continued

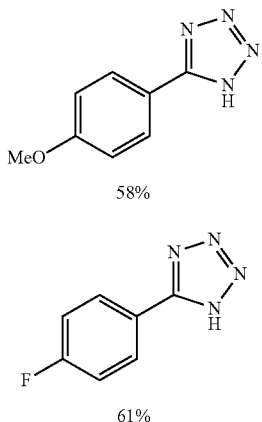

(7d) 58%

(7e) 61%

Synthesis of Some Phenyl Ring Substituted 1H Tetrazoles

Reactions have been Performed Under Microwave Irradiation Using QuF (4) Catalyst Hygroscopic nature of ionic salts is well-known. The presence of water contents in ionic liquids affects their catalytic efficacy. Keeping in view this fact, we performed click reaction with freshly prepared QuF-$C_5$ (4), dried over anhydrous magnesium sulfate, by adding different percentage of water (10%, 30%, and 50%) in reaction mixture. All these reactions were performed under microwave irradiation to elaborate the effects of added water contents on the catalytic efficiency of ionic liquid (4). The yield of 5-(p-methylphenyl)-1H-tetrazole (7a), in the presence of 0% and 10% water was found to be almost the same (60% and 58% respectively), while with 30% water content, the reaction output slightly dropped to 45%. A substantial decline in reaction output (32%) was observed in the presence of 50% water (FIG. 1). The percentage of water in ionic liquid (4) was determined by using Karl-Fisher apparatus after storing more or equal to 3 months at room temperature. The water contents in (4) were found to be 12.3%. These observations signify the tolerance level of water in catalytic efficiency of quinoline fluoride salts. The catalytic efficiency of QuFs. (4) or (5) was further explored by preforming a one-pot reaction involving 1) Knoevenagel condensation, and subsequent 2) dimerization of Knoevenagel product (9) under solvent-free conditions (Scheme-3). The reaction sequence showed proton abstraction from methylene group with QuF and reaction of resultant malononitrile anionic species to acetophenone (8) to afford alkylidene malononitrile species (9). In second step, QuF again abstracts proton from α-methyl group to promote dimerization via multistep sequence to afford 2-dicyanomethylene-6-methyl-4,6-bis(m-methoxyphenyl)-1,2,5,6-tetrahydronicotinonitrile (13) (Scheme-3). Moreover, a reaction between acetylacetonate (13) and p-methoxyphenyl hydrazine hydrochloride (14) in the presence of QuF (4) under solvent-free condition afforded corresponding 3,5-dimethyl-1-(p-methoxyphenyl)-1H-pyrazole (15) in good yield (63%) as shown in the Scheme-4. The applications of QuFs in 1H tetrazole (7), 1,2,5,6-tetrahydronicotinonitrile (12) or pyrazole (15) formation signify their catalytic activity in organic reactions. Structure of 2-dicyanomethylene-6-methyl-4,6-bis(m-methoxyphenyl)-1,2,5,6-tetrahydronicotinonitrile (12) was fully characterized with $^1H$, $C^{13}$ NMR and correlation spectra (HSQC, HMBC, COSY, NOSEY).

Scheme-3: Solvent-Free one-pot Knoevenagel condensation and dimerization to (12)

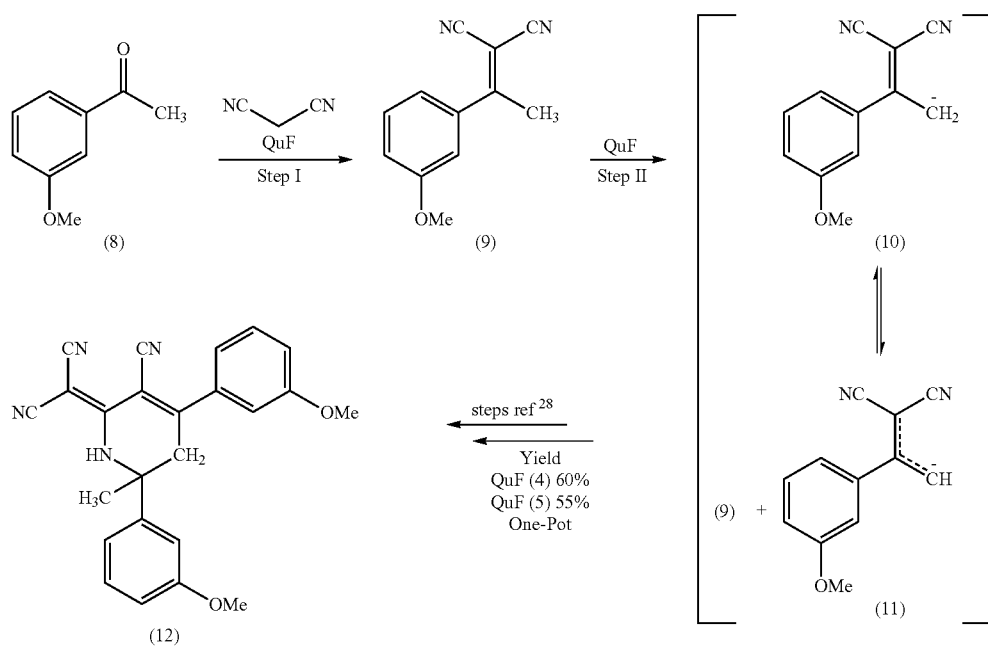

Scheme-4: Synthesis of 3,5-dimethyl-1-(p-methoxyphenyl)-1H-pyrazole (15)

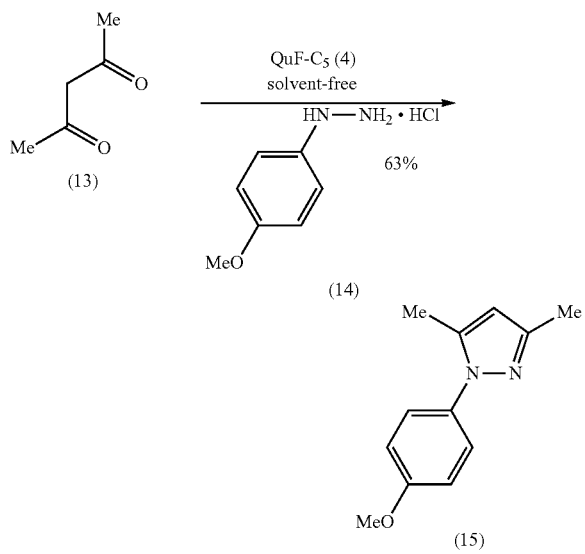

Thermal Studies

Figure 2:
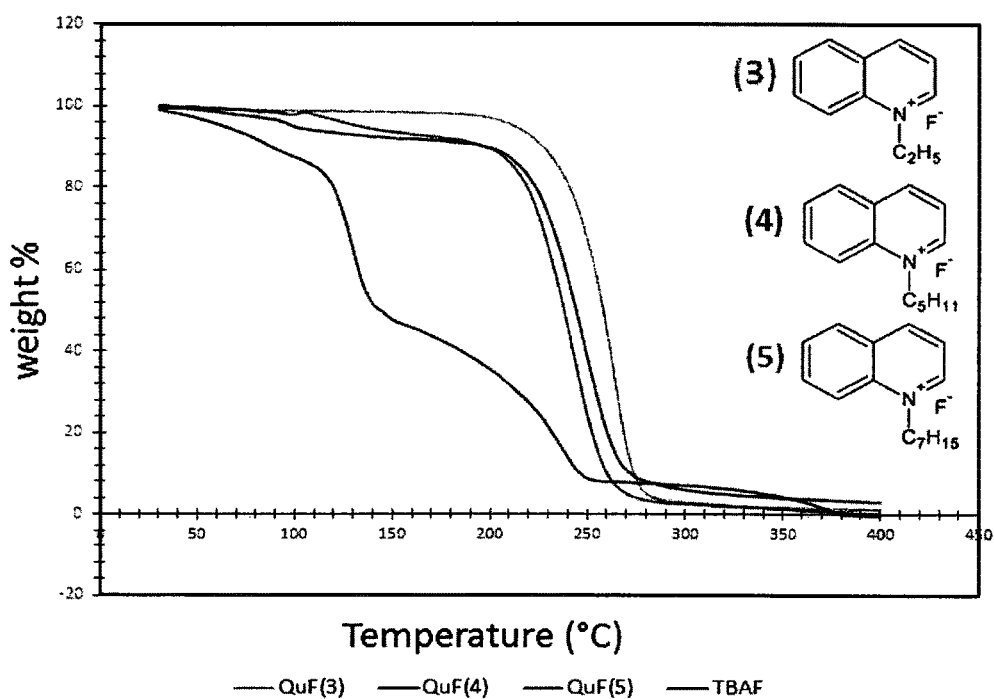
FIG. 2 depicts TGA graphs of ionic salts (3), (4), (5), and TBAF.$3H_2O$.
Figure 3A:
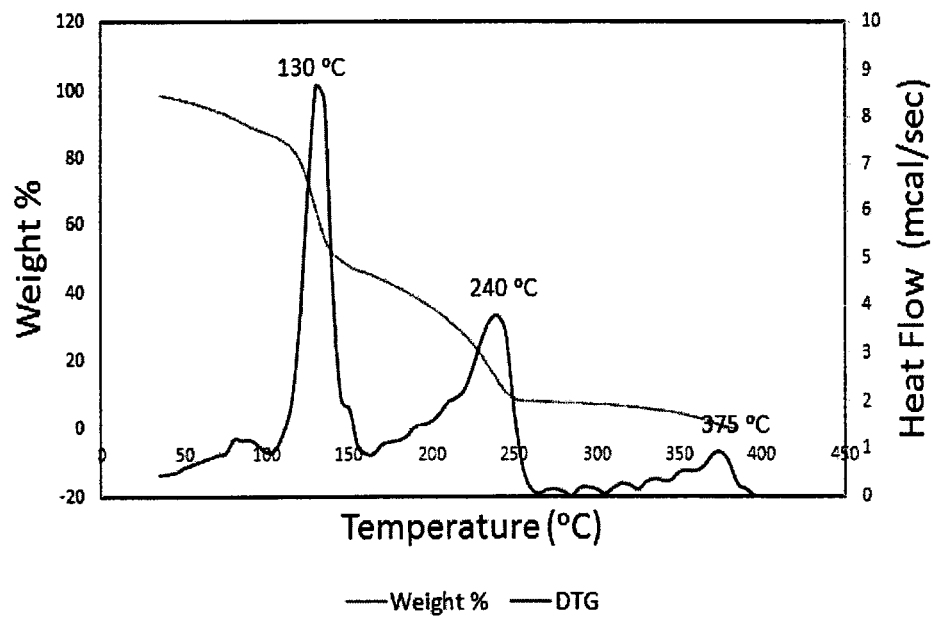
FIG. 3A depicts TBAF.$3H_2O$ TGA and DSC graphs.
Figure 3B:
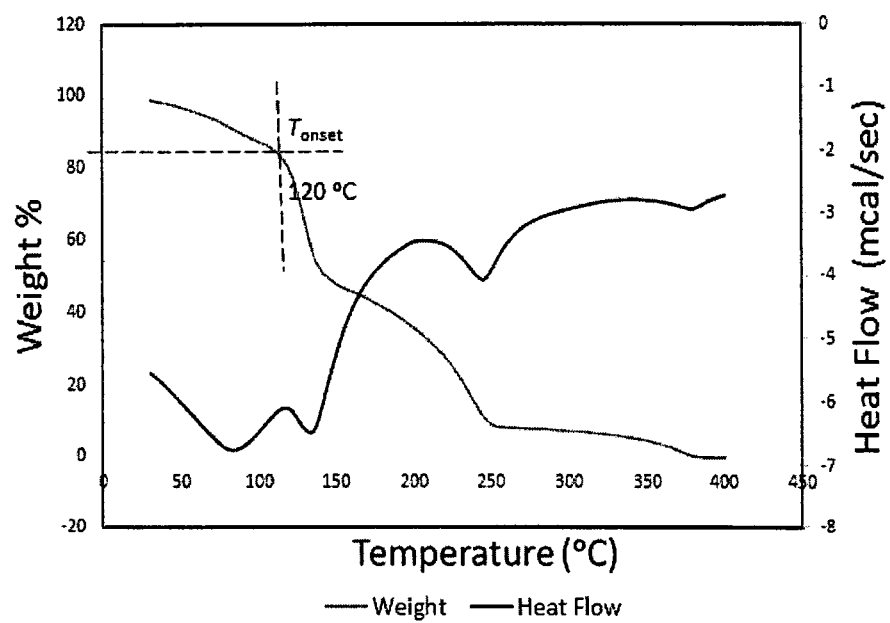
FIG. 3B depicts TGA and first derivative (DTG).

Thermal studies were also carried out for all newly synthesized QuFs (3, 4, and 5) along with commercially available TBAF.3H$_2$O to determine their decomposition temperatures. FIG. 2 shows overlap of thermo gravimetric analysis (TGA) graphs of all QuFs (3, 4, and 5) and TBAF.3H$_2$O. TGA graph of showed TBAF decomposition in three steps, the first step (20% weight loss) is due to loss of water molecules when heated from ambient to 120° C., the remaining steps 120° C. to 165° C. (35% weight loss), and 165° C. to 260° C. (37% weight loss) are due to successive loss of alkyl chains possibly involving a Hofmann elimination.[30] Hofmann elimination has been proposed to be the most plausible mechanism for thermal degradation of quaternary ammonium compounds containing alkyl chains. In last step, slight weight loss of 4% is observed in the range 350° C. to 380° C. The differential scanning calorimetry (DSC) data has been overlapped on TGA graph of TBAF, indicating an endothermic peak associated with each weight loss step. Derivative thermo gravimetric or first derivative graph (DTG) was calculated for TBAF and is shown in FIG. 3b. The DTG peaks indicate two decomposition temperature for TBAF at 130° C. and 240° C.

Figure 4A:
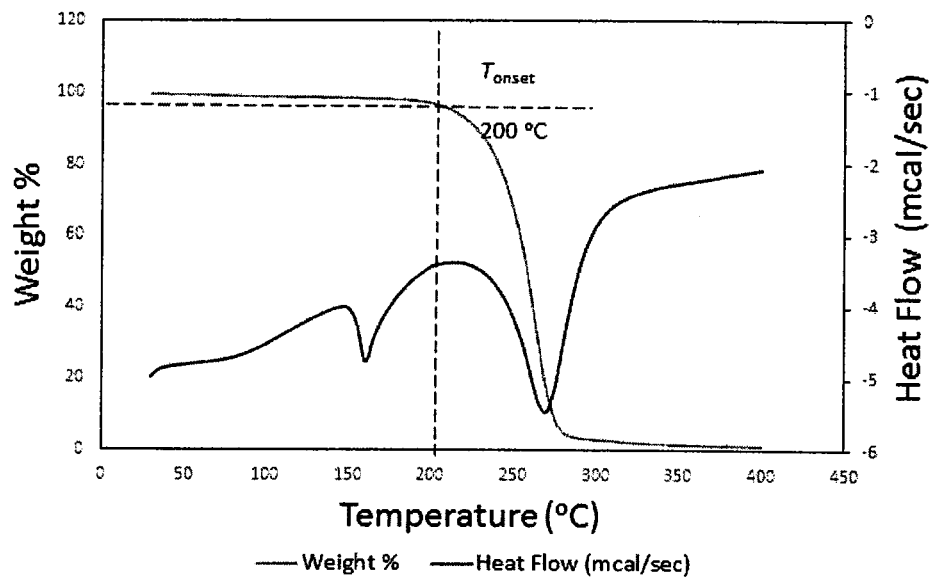
FIG. 4A depicts TGA and DSC graphs of QuF (3).
Figure 4B:
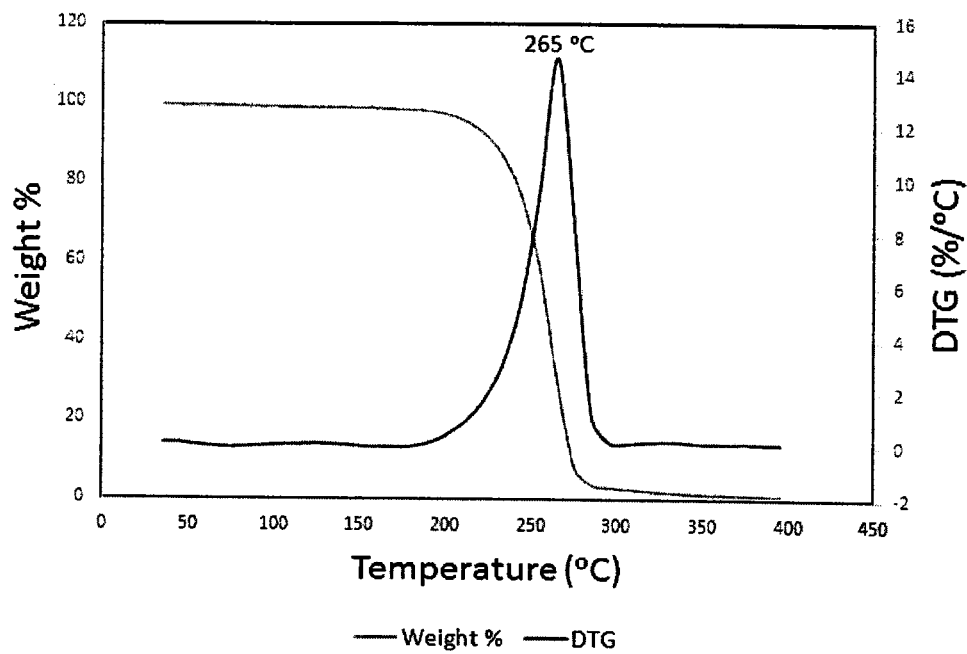
FIG. 4B depicts TGA and first derivative (DTG) of QuF (3).

The ionic liquid QuF (3) was found to possess most thermal stability, the onset of decomposition (T$_{onset}$) was observed at 200° C., which is the highest among all QuF ionic salts studied, including the commercially available TBAF.3H$_2$O. The ionic liquid (3) decomposes in a single step in the temperature range 200° C. to 300° C. (95% weight loss). First derivative graph of TGA data (DTG) was also calculated and overlapped on TGA graph (FIG. 4a), indicating decomposition temperature at 265° C. (which is 10 degrees higher than (4), 20 degrees higher than (5), and 135 degrees higher than first decomposition temperature of TBAF). The heat flow data (differential scanning calorimetry, DSC) has also been overlapped on TGA data, it indicates two endothermic peaks, the first one is observed in the temperature range 150-175° C., since there is no associated weight loss step in this temperature range, it is inferred that this endothermic peak is due to melting of (3). The second endothermic peak is observed in the temperature range 245-300° C. and is due to decomposition since it has as associated weight loss with it (TGA data). An overlay of TGA graph with DTG graph showed decomposition at 265° C. (FIG. 4b).

Figure 4C:
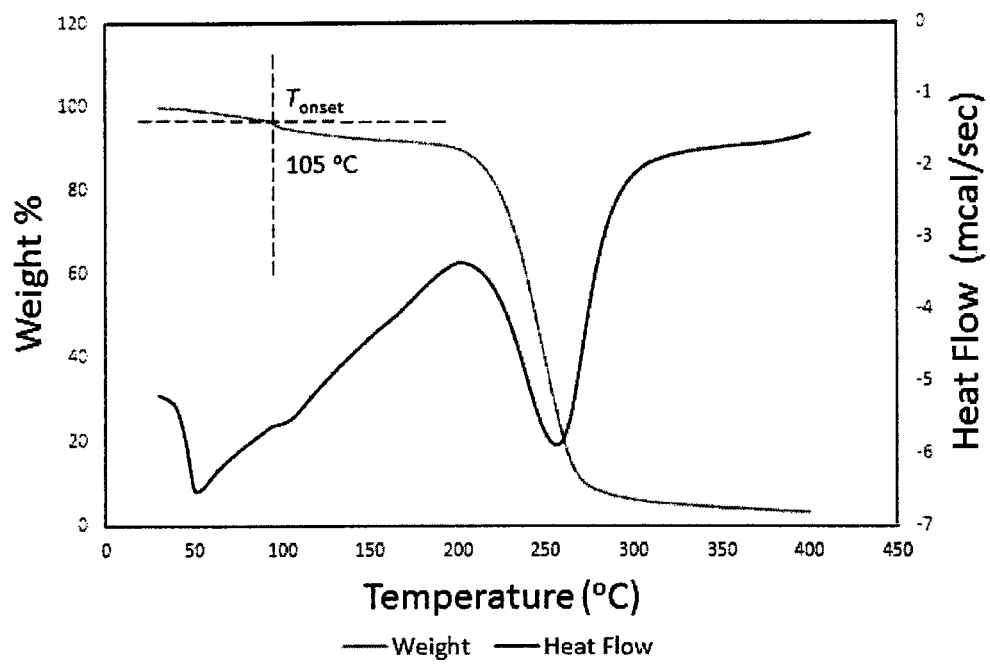
FIG. 4C depicts TGA and DSC graphs of QuF (4).
Figure 4D:
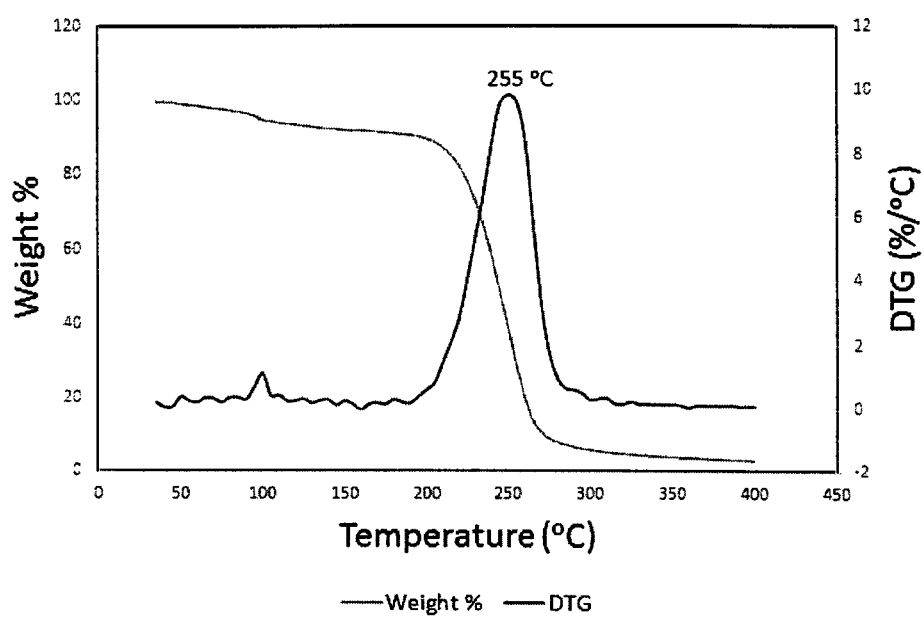
FIG. 4D depicts TGA and first derivative (DTG) of QuF (4).

For QuF (4), the first step in TGA is observed in the temperature range from ambient to 100° C. (6% weight loss), and is due to dehydration, this is also evidenced by accompanying endothermic peak in the same temperature range. The onset temperature (T$_{onset}$) is calculated after dehydration step and is 105° C. (FIG. 4c). From 105-200° C., there is a slight and gradual loss of weight (6%), the last and major step in TGA is observed in the broad temperature range of 200-315° C. (86% weight loss) and indicates decomposition as evidenced by an associated endothermic peak in the matching temperature range. First derivative graph of TGA data (DTG) was also calculated and overlapped on TGA, indicating decomposition temperature at 255° C. (FIG. 4d).

Figure 4E:
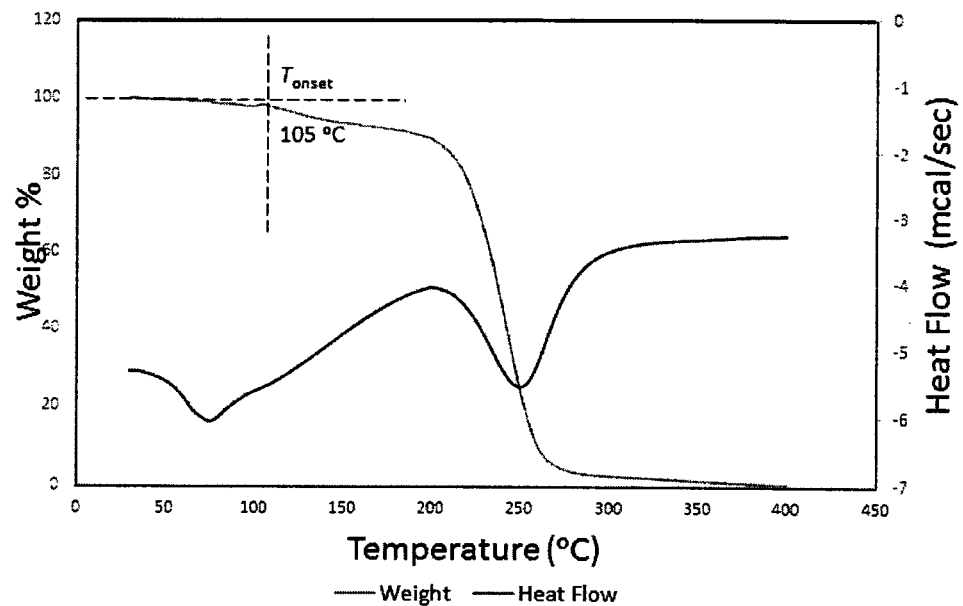
FIG. 4E depicts TGA and DSC graphs of QuF (5).
Figure 4F:
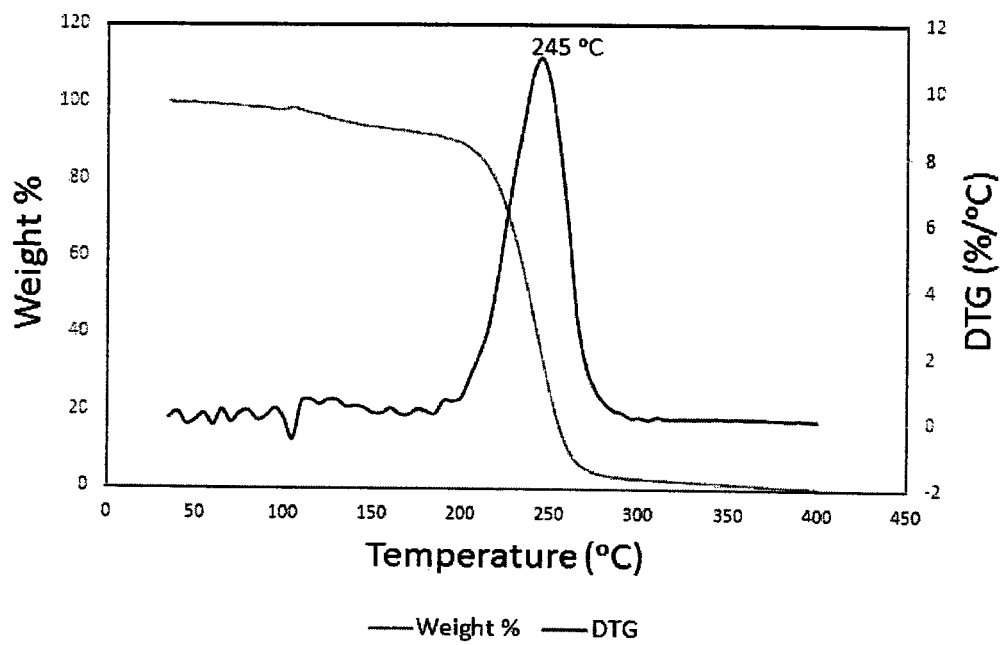
FIG. 4F depicts TGA and first derivative (DTG) of QuF (5).

Thermal analysis of QuF (5) was very similar to (3). In TGA graph for (5), there is a very slight loss in weight (2% weight loss) in the beginning from ambient temperature to 110° C., this step is accompanied by a small endothermic peak (as evidenced from the heat flow, DSC data overlapped on TGA graph). This slight loss is most probably due to dehydration. The onset temperature (T$_{onset}$) is calculated after dehydration step and is 110° C. (FIG. 4e). From 110-200° C., there is a gradual loss of weight (8%), whereas the majority of the weight loss (88%) is observed in the temperature range 200-350° C. This weight loss step is due to decomposition as it is accompanied by a corresponding endothermic peak (FIG. 4e). First derivative graph of TGA (DTG) was also calculated and overlapped on TGA, indicating decomposition temperature at 245° C. (FIG. 4f).

Theoretical Studies—Bulk Properties

Figure 5:
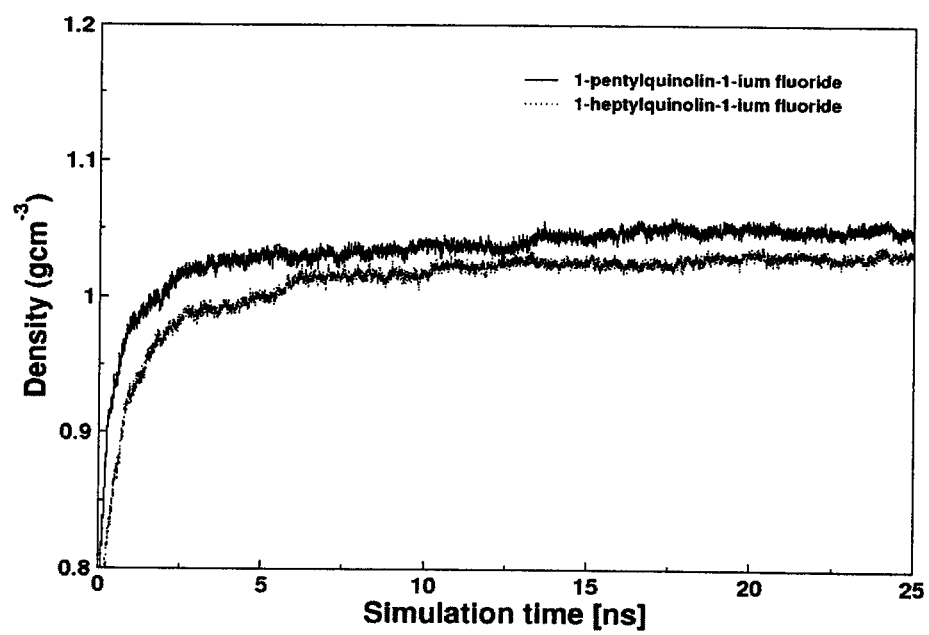
FIG. 5 shows densities of QuFs (4) and (5) ionic liquids calculated by molecular dynamics simulations.

Molecular dynamics simulations were performed to evaluate the bulk properties of QuFs based ionic liquids such as density, structural and transport properties. The densities of QuFs (4) and (5) ionic liquids were obtained from molecular dynamics simulations at 300 K as depicted in FIG. 5. A sufficiently long simulation (25 ns) including 05 ns of equilibration was considered essential for the evaluation of the density of the ionic liquid at 300 K. The average densities of QuFs (4) and (5) were computed between 1.04±0.003 and 1.02±0.002 g/cm$^3$, respectively indicating a non-significant difference between densities of the two liquids. This could be attributed to the similar chemical architecture of the compounds having minor difference of alkyl chain attached to the quinolinium ion. The calculated values for densities may deviate from experimental values, since an accurate value of experimental density is not available. The deviation in the calculated densities could be resulted as generalized amber force fields were utilized in the simulations. Improvement in the calculated densities of these ionic liquids may be obtained by using more refined non-bonding parameters, since it was previously reported that they could be derived from experimental densities of similar compounds.

Figure 6:
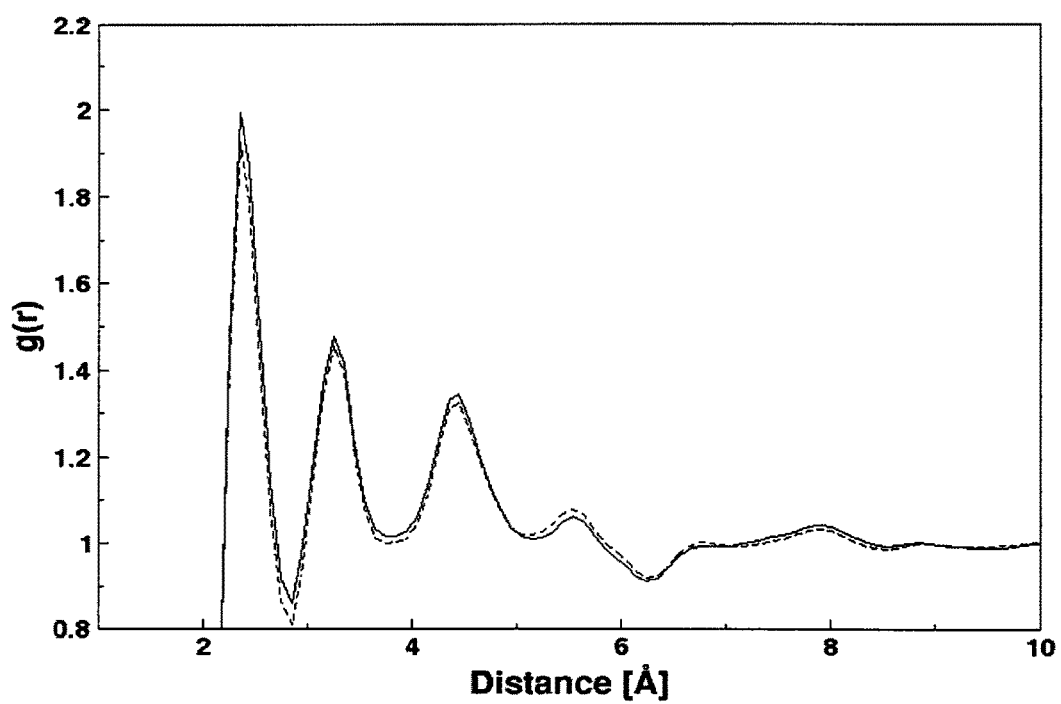
FIG. 6 shows radial distribution functions between center of masses of cation and anion in both ionic liquids (Solid and Dash line are for QuFs (4) and (6), respectively).

The structural properties of the QuF ionic liquids were assessed via site-site intermolecular radial distribution functions as shown in FIG. 6-7. The radial distribution functions plotted between center of mass of the cation and anion exhibit an identical plot for both compounds (cf. FIG. 6). In case of QuF (4), a sharp first peak appeared at 2.35 Å which leads to respective second and third well-structured peaks at 3.25 and 4.45 Å along with further oscillations extending beyond 10 Å. A closely related radial distribution function pattern was observed in case of QuF (5) indicating a similar structure for the two ionic liquids. The sharp first peaks in both RDFs demonstrate that a strong electrostatic interaction which exists between a pair of cation and anion whereas second and third peaks correspond to electrostatic interaction that may be experienced between cations and anions of different ion pairs.

Figure 7A:
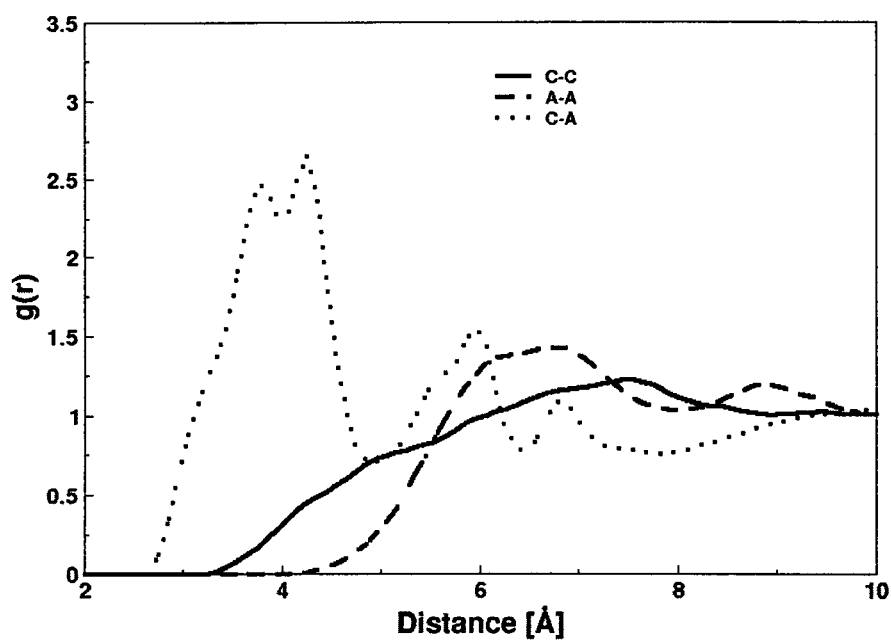
FIG. 7A shows radial distribution functions between the N atom of cations (C-C), between the fluoride anions (A-A), and between the N atoms of cations and fluoride anions (C-A) of the QuF (4) ionic liquid are illustrated.
Figure 7B:
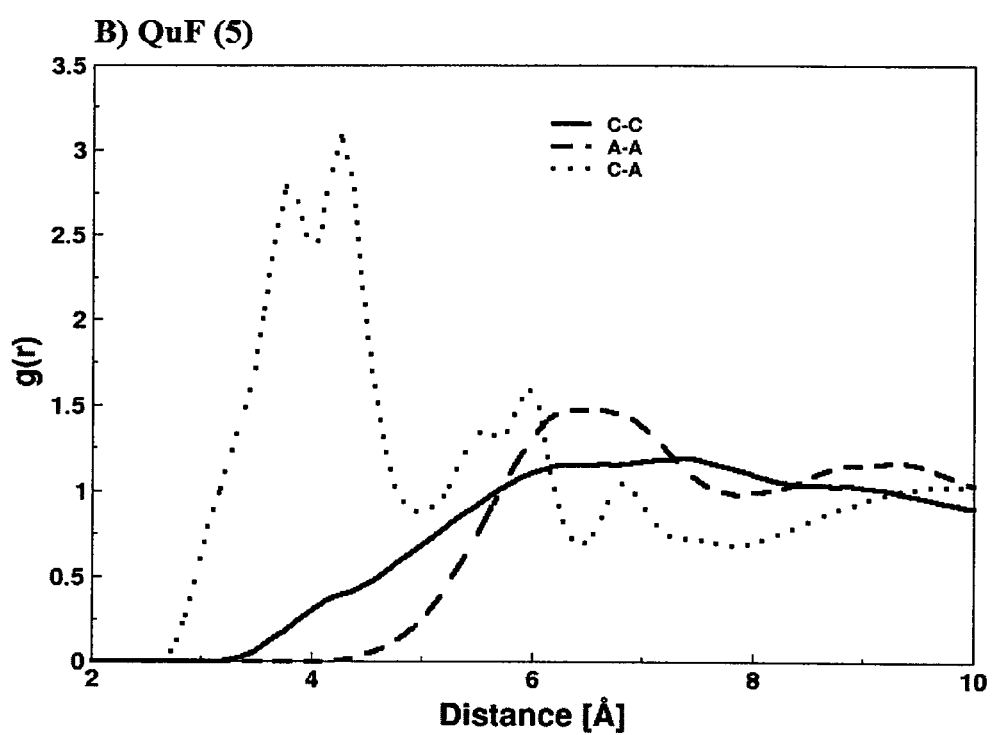
FIG. 7B shows radial distribution functions between the N atom of cations (C-C), between the fluoride anions (A-A), and between the N atoms of cations and the nitrogen atom of the fluoride anions (C-A) of the QuF (5) ionic liquid are illustrated.

FIG. 7a displays radial distribution functions between atomic pairs of cations and anions in QuF (4) ionic liquids. The distribution function between the nitrogen atoms of the quinolinium ion ($g_{C-C}$) shows a very broad unstructured peak whose maximum appeared at a larger distance, after that between fluoride ions ($g_{A-A}$) located beyond 7 Å. The distribution function evaluated between nitrogen atom of quinolinium cation and fluoride anion ($g_{C-A}$) was visible at a lower distance compared to that of $g_{C-C}$ and $g_{A-A}$ which is a clear indication of the charge-ordering structure due to electrostatic force of attraction. In $g_{C-A}$ profile, the splitting of first broad peak resulted into two tiny peaks located at 3.77 and 4.24 Å that were attributed to the delocalization of positive charge between nitrogen and adjacent carbon connected via unsaturated bond, thereby dynamically binding fluoride anion to the nitrogen and carbon atom. For QuF (5), a similar behavior was observed as depicted by radial distribution functions shown in FIG. 7b. This clearly indicates that increasing alkyl chain length does not cause any influence on the structural characteristics of QuF based ionic liquids in bulk.

Figure 8A:
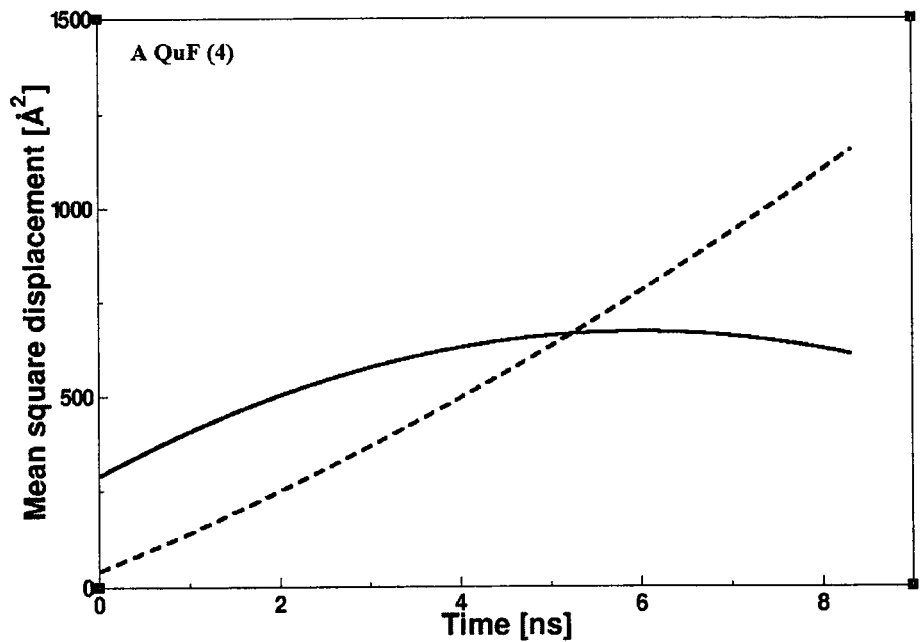
FIG. 8A shows mean-square displacements (MSDs) of the ions in the QuF (4) (black and dotted lines for the cation and anion, respectively).
Figure 8B:
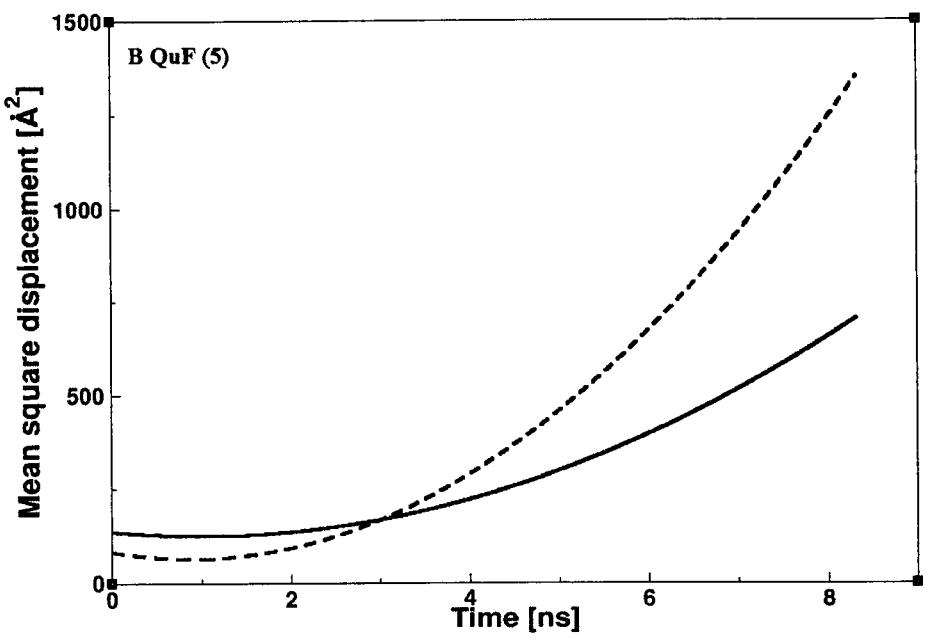
FIG. 8B shows the mean-square displacements (MSDs) of the ions in the QuF (5) (black and dotted lines for the cation and anion, respectively).

The mean square displacements (MSDs) of the cations and anions in the QuFs (4) and (5), computed from 25 ns simulations are shown in FIG. 8a-8b. Contrasting to similar structural properties for the two ionic liquids, the dynamical properties i.e. transport properties in terms of MSDs of these liquids are different which clearly demonstrate the influence of two alkyl chains of different length attached to the quinolinium nitrogen that in turn affect the MSDs of fluoride anion. The MSD plots have asymptotic linear region till 2 ns that corresponds to their diffusion properties, hence self-diffusion coefficients of the cation and anions are possible to compute from MSDs of the ions over this region between 0 and 2 ns according to the Einstein relation.

$$2nD = \lim_{t \to \infty} \frac{MSD}{t}$$

Where n is the number of dimensions which is equal to 3 and D stands for Diffusion Coefficient. The self-diffusion coefficients for the ions in the QuF (4), calculated from the fittings of the MSD slope's over 0-2 ns, are $6.42 \pm 0.25 \times 10^{-7}$ and $22.31 \pm 0.11 \times 10^{-7}$ cm$^2$/s for the cations and anion, respectively. In case of QuF (5), very deviating values were obtained for the self-diffusion coefficients ($11.39 \pm 0.26 \times 10^{-7}$ and $25.33 \pm 0.55 \times 10^{-7}$ cm$^2$/s for the cation and anion, respectively). Substantial differences were found between self-diffusion coefficients for QuF (4) and (5) and it is also noteworthy to mention that in both cases, anions have larger values of self-diffusion coefficients compared to the cations. The deviations calculated with the diffusion coefficients may vary and are prone to some sort of minor statistical errors, since under and overestimation in the values could happen due to utilization of different force field models for the simulation studies.

Stability of QuFs (3, 4, and 5) Compounds

It has already been reported that the long-term thermal stability of ionic liquids serves an opportunity to explore the applicability of ionic liquids in a number of industrial processes. The evaluation of binding energies of these compounds enabled to establish their thermal stabilities which were obtained by applying DFT calculations on QuF derivatives. Table-2 showed data for the binding energies of the QuF derivatives in comparison to the TBAF compound (−104.25 kcal/mol) which has higher value than that of QuF derivatives.[24] The binding energy computed for QuF (3) was found −126.6 kcal/mol which indicates strong association of cation and anion that slightly diminishes with increasing length of alkyl side chain as indicated from the values of binding energies of QuFs (4) and (5), respectively. Closely matched data of binding energy was obtained for QuFs (4) and (5), indicating that the increased length of alkyl chains does not cause significant variations in the binding energies of QuF ionic liquids (Table-2).

TABLE 2

| Binding energies calculated for QuFs ionic liquids obtained from density functional theory calculations | | | | |
|---|---|---|---|---|
| QuFs | 3 | 4 | 5 | TBAF |
| Energy (kcal/mol) | −126.6 | −125.2 | −124.9 | −104.25 |

The relationship between the ionic structure and the transport properties of the ionic liquids needs to be figured out, since it aids significantly in designing novel ionic liquids for many industry related applications. Based on simulation data, it was evaluated that a direct relationship between self-diffusion coefficients and binding energies of the ion pairs lead a conclusion that several factors such as size of cations, magnitude of binding energies for the ion pairs (cations and anion) determine the magnitude of the self-diffusion coefficients. The radial distribution functions exhibited somewhat similar attributes which is an indication of similar charge-order structures for these ionic liquids. Besides, structural properties, it also seems significant to mention that the binding energies of both ionic liquids (4 and 5) are identical, though the transport properties are strongly dependent on the alkyl chain length, hence indicating that the transport properties rely on size of cations. Other properties such as size of anions, interaction between cation and anions, etc. also affect the ion diffusion but in QuF based ILs fluoride anions are present in both cases. It was previously reported about the dependence of the self-diffusion coefficients on the alkyl chain length—long alkyl chain decreases and increases the self-diffusion coefficients of the ILs when they are composed of other anions. Here, a variation in the alkyl chain length affects the self-diffusion properties, thus showing influence on the fluid properties of the ionic liquids.

In conclusion, quinoline-based ionic fluoride salts (QuFs) (3, 4, and 5) have been synthesized and explored as catalysts in different organic reactions. 5-(p-Methylphenyl)-1H-tetrazole (7), 2-dicyanomethylene-6-methyl-4,6-bis(m-methoxyphenyl)-1,2,5,6-tetrahydronicotinonitrile (12), and 3,5-dimethyl-1-(p-methoxyphenyl)-1H-pyrazole (15) have been synthesized from their corresponding precursors by using QuFs as catalyst under solvent-free conditions. Thermal stability of the QuFs (3, 4, and 5) has also been determined by conducting TGA, DTG, and DSC analysis. Data obtained after molecular dynamics simulations and binding energy calculations is significant enough to be considered or addressed in the context of future design of novel ionic liquids.

Theoretical Methods; Density Functional Theory (DFT) Studies

Density functional methods were applied to QuF derivatives to compute their binding energies. This was performed in order to understand the effect of alkyl chain of different lengths on the stability of these compounds. Molecular structures of these derivatives were optimized without applying symmetry constraints at DFT level of theory using B3LYP (Becke, three-parameter, Lee-Yang-Parr) functional along with 6-31G+(d, p) basis set for all atoms. The binding energies for these ionic compounds were calculated using the optimized structures in comparison to that of TBAF.[33] Gaussian 09 software[35] was used for all these calculations.

Molecular Dynamics Simulations

Figure 9:
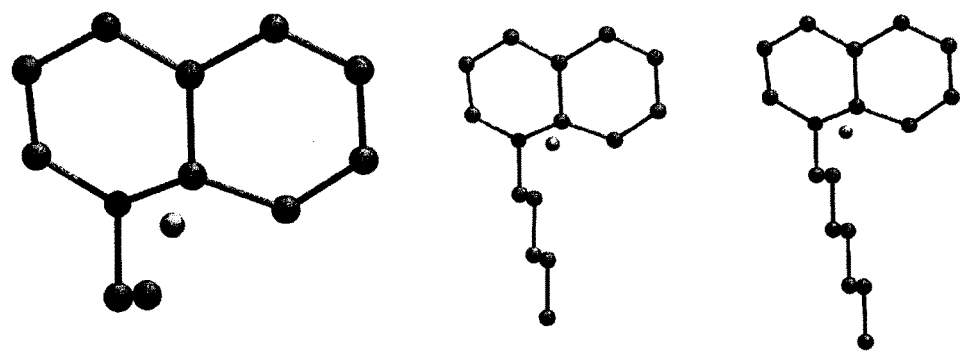
FIG. 9 shows cations and anion of QuFs (3), (4), and (5).
Figure 10:
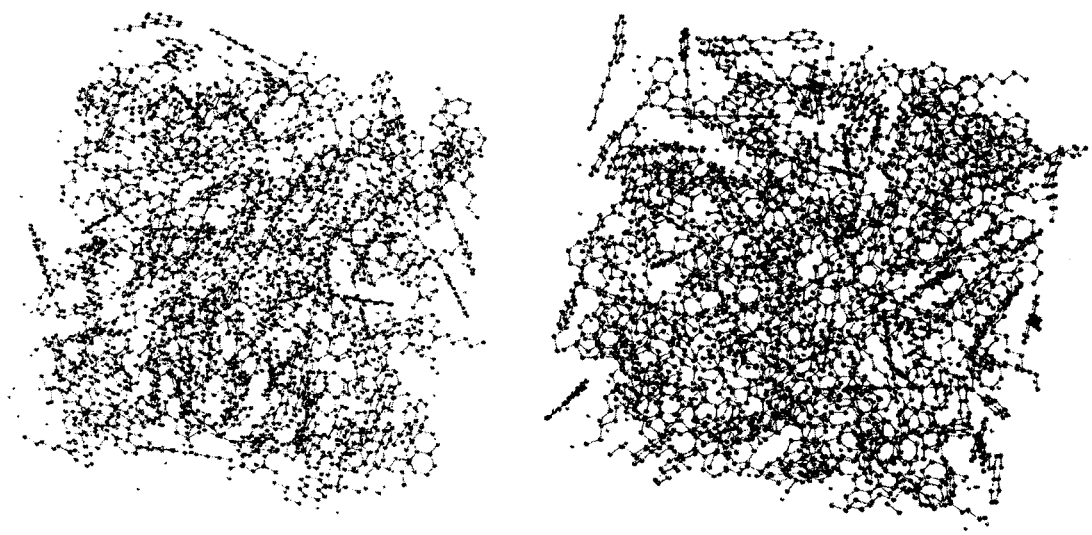
FIG. 10 shows simulation boxes representing QuFs (4) and (5).

The optimized geometries of QuF derivatives obtained from ab initio calculations are shown in FIG. 9. The QuF derivatives (4) and (5) were modeled with Generalized Amber Force Field (GAFF) and Restrained Electrostatic Potential (RESP) charges were calculated according to the method reported in the literature. QuF derivatives were packed into a simulation box consisting of 200 ion pairs in defined regions of space by employing Packmol program, thus resulting in two simulation systems as illustrated in FIG. 10.

Molecular dynamics simulations for both systems were performed in the NPT ensemble. To remove bad clashes, energy minimizations of both systems were performed for 10,000 steps which were followed by NVT equilibration for 5 ns. The equilibrated systems were then subjected to sampling of trajectories for 25 ns. All bonds including hydrogen bonds were treated flexible, enabling a time step of 1.0 fs. Particle mesh Ewald algorithm was employed to treat long-range electrostatic interactions, and a cutoff value of 8.0 Å was set for non-bonded interactions. The temperature was kept at 298 K employing the Langevin dynamics using a collision frequency of 5.0 ps$^{-1}$. The pressure was maintained at 1 atm utilizing pressure coupling algorithm with a relaxation time of 1.0 ps. For both simulations, SANDER module implemented in AMBERTOOLS14 was used whereas CPPTRAJ and VMD were used for the analysis and visualization of trajectories, respectively.

EXAMPLE 1

General Synthetic Procedure for Quinoline-Based Fluoride Ionic Liquids (3-5)

Step I:

To an oven dried round bottom flask quinoline (3-5 g, 23-39 mmol, 1 equiv.), alkyl halides (I, Br) (1.0-1.2 equiv.) (ethyl iodide 3.59 g, 23 mmol or 1-bromopentane 7.02 g, 46.8 mmol or 1-bromoheptane 8.33 g, 46.8 mmol) along with 2-3 mL of toluene at room temperature. The resulting reaction mixture was heated at reflux (120-125° C.) until thin layered chromatographic analysis showed no starting material, quinoline 1. The resulting corresponding ionic liquids was further washed with cold toluene or hexane, dried and used without purification in the next step.

Step II:

In fluoride exchange step, the crude mixture of step I was dissolved in methanol (5 mL) and added to the saturated aqueous solution of KF (5 mL) at room temperature. The mixture was stirred overnight, afterwards methanol was evaporated. To the aqueous layer, dichloromethane (15 mL) was added and both layers were separated using a separating funnel. The organic layer was dried over magnesium sulfate, filtered, and evaporated by using rotary evaporator. The obtained material was occasionally washed with hexane to get the final desired product. The final ionic quinoline-based ionic salts 3-5 were characterized with $^1$H, $^{13}$C-NMR, IR, UV spectroscopy and mass spectrometry.

Spectral Data of Quinoline-Based Fluoride Salts

1-Ethylquinolin-1-ium fluoride (3): Brown solid, (3.86 g, 95%), IR ($v_{max}$, cm$^{-1}$): (Solid, KBr) 3450, 3055, 3018, 2974, 1593, 1523, 1445, 1375, 1213, 1164, 1134, 1087, 981, 923, 873, 806, 773, 739, 704, 569, 534, 480, 422. $^1$H NMR (400 MHz, DMSO): $\delta_H$ 9.55 (1H, d, J=5.2 Hz, ArH), 9.27 (1H, d, J=8.4 Hz, ArH), 8.61 (1H, d, J=9.2 Hz, ArH), 8.48 (1H, d, J=8 Hz, ArH), 8.27 (1H, app td, J=8.4, 0.8 Hz, ArH), 8.18 (1H, dd, J=8.4, 6.0 Hz, ArH), 8.05 (1H, t, J=7.4 Hz, ArH), 5.09 (2H, q, J=7.2 Hz, CH$_2$), 1.61 (3H, t, J=7.2 Hz, CH$_3$); $^{13}$C NMR (100 MHz, DMSO): $\delta_C$ 149.3 (CH), 147.2 (CH), 137.2 (C), 135.6 (CH), 130.7 (CH), 129.8 (CH), 129.6 (C), 122.3 (CH), 118.8 (CH), 52.9 (CH$_2$), 15.2 (CH$_3$). MS-ESI m/z (%), 158.1 (M$^+$-F$^-$, 100); ESI-HRMS (M$^+$-F$^-$) C$_{11}$H$_{12}$N Found 158.0956, Calculated 158.0969.

1-Pentylquinolin-1-ium fluoride (4): Dark Brown thick oil, (6.82 g, 80%), IR ($v_{max}$, cm$^{-1}$): (Solid, KBr) 3429, 3065, 3020, 2956, 2929, 2864, 1624, 1593, 1528, 1460, 1373, 1232, 1163, 1034, 822, 777, 744, 584, 544, 468. $^1$H NMR (400 MHz, DMSO): $\delta_H$ 9.59 (1H, d, J=5.2 Hz, ArH), 9.29 (1H, d, J=8 Hz, ArH), 8.62 (1H, d, J=9.2 Hz, ArH), 8.49 (1H, d, J=8.4 Hz, ArH), 8.27 (1H, t, J=7.8 Hz, ArH), 8.18 (1H, dd, J=8, 5.6 Hz, ArH), 8.05 (1H, t, J=7.6 Hz, ArH), 5.06 (2H, t, J=7.2 Hz, CH$_2$), 1.97 (2H, quin, J=7.0 Hz, CH$_2$), 1.38-1.30 (4H, m, (CH$_2$)$_2$), 0.85 (3H, t, J=6.8 Hz, CH$_3$); $^{13}$C NMR (125 MHz DMSO): $\delta_C$ 149.6 (CH), 147.3 (CH), 137.3 (C), 135.6 (CH), 130.7 (CH), 129.8 (CH), 129.6 (C), 122.1 (CH), 118.9 (CH), 57.2 (CH$_2$), 29.2 (CH$_2$), 27.8 (CH$_2$), 21.6 (CH$_2$) 15.2 (CH$_3$). MS-ESI 200.1 (M$^+$-F$^-$, 100); EI-HRMS (M$^+$) C$_{14}$H$_{18}$NF Found 219.1435 Calculated 219.1423; ESI-HRMS (M$^+$-F$^-$) C$_{14}$H$_{18}$N Found 200.1435, Calculated 200.1439.

1-Heptylquinolin-1-ium fluoride (5): Dark brown oil, (7.51 g, 78%), IR ($v_{max}$, cm$^{-1}$): (Solid, KBr) 3429, 3064, 3020, 2928, 1624, 1593, 1528, 1460, 1373, 1234, 1161, 821, 777, 545, 470. $^1$H NMR (400 MHz, DMSO): $\delta_H$ 9.56 (1H, d, J=5.2 Hz, ArH), 9.28 (1H, d, J=8.4 Hz, ArH), 8.61 (1H, d, J=9.2 Hz, ArH), 8.49 (1H, d, J=8.4 Hz, ArH), 8.28 (1H, t, J=8 Hz, ArH), 8.18 (1H, dd, J=8.4, 5.8 Hz, ArH), 8.05 (1H, t, J=7.6 Hz, ArH), 5.05 (2H, t, J=7.6 Hz, CH$_2$), 1.96 (2H, quin, J=7.4 Hz, CH$_2$), 1.39-1.23 (8H, m, (CH$_2$)$_4$), 0.84 (3H, t, J=6.8 Hz, CH$_3$); $^{13}$C NMR (75 MHz, DMSO): $\delta_C$ 149.6 (CH), 147.4 (CH), 137.4 (C), 135.6 (CH), 130.7 (CH), 129.8 (CH), 129.7 (C), 122.1 (CH), 118.9 (CH), 57.3 (CH$_2$), 30.9 (CH$_2$), 29.4 (CH$_2$), 28.1 (CH$_2$) 25.7 (CH$_2$), 21.9 (CH$_2$) 13.8 (CH$_3$). MS-ESI 228.2 (M$^+$-F$^-$, 100); ESI-HRMS (M$^+$-F$^-$) C$_{16}$H$_{22}$N Found 228.1752 Calculated 228.1752.

EXAMPLE 2

Procedure for 5-(p-methylphenyl)-1H-tetrazole (7a-e) Synthesis

In a typical reaction, an oven dried micro reaction vessel capped with septum was used for reaction. To an open vessel, 4-methyl benzonitrile (234 mg, 1 or 2 mmol, 1 equiv.), trimethyl silyl azide (460 mg, 4 mmol, 2 equiv.) along with quinoline fluoride salt(s) (4) 438 mg, 2 mmol, 1 equiv.) was added at room temperature. The resulting reaction mixture was heated under convention heating at 105-110° C. for 6 h until TLC showed no starting material. The click reaction was also carried out under microwave-irradiation at 120° C. for 2 h. The reaction mixture in both cases was cooled to room temperature and quenched with 1M HCl (15 mL). To this mixture, EtOAc (20 mL) was added and organic layer was separated via a separating funnel, dried over MgSO$_4$, filtered and evaporated in rotary evaporator to get the crude material. Silica gel column chromatography was used to separate the pure 1H-tetrazoles (7a-e) as off-white solids in 50-60% yield. 5-(4'-methylphenyl)-1H-tetrazole (7a) 60% (192 mg) $^1$H NMR (400 MHz, DMSO): $\delta_H$ 7.91 (2H, d, J=8.0 Hz, ArH), 7.39 (2H, d, J=8.0 Hz, ArH), 2.38 (3H, s, CH$_3$); MS-EI m/z 160 (M$^+$). The data is identical to those previously reported.[41,42]

5-(3'-Methylphenyl)-1H-tetrazole: (7b) 65% (105 mg) $^1$H NMR (400 MHz, DMSO): $\delta_H$ 7.86 (1H, brs, ArH), 7.81 (1H, d, J=7.6 Hz, ArH), 7.47 (1H, t, J=7.8 Hz, ArH), 7.39 (2H, d, J=7.6 Hz, ArH), 2.39 (3H, s, CH$_3$); MS-EI m/z 160 (M$^+$).

5-(4'-Chlorophenyl)-1H-tetrazole (7c):[43] 69% (125 mg) $^1$H NMR (400 MHz, DMSO): $\delta_H$ 8.03 (2H, d, J=8.8 Hz, ArH), 7.67 (2H, d, J=8.4 Hz, ArH); MS-EI m/z 180 (M$^+$).

5-(4'-Methoxyphenyl)-1H-tetrazole (7d): 58% (102 mg) $^1$H NMR (400 MHz, DMSO): $\delta_H$ 7.96 (2H, d, J=8.8 Hz, ArH), 7.13 (2H, d, J=8.8 Hz, ArH), 2.83 (3H, s, OCH$_3$); MS-EI m/z 176 (M$^+$).

5-(4'-Fluorophenyl)-1H-tetrazole (7e):[44] 61% (100 mg) $^1$H NMR (400 MHz, DMSO): $\delta_H$ 8.06 (2H, dd, J=5.2, 8.8 Hz, ArH), 7.45 (2H, t, J=8.8 Hz, ArH); MS-EI m/z 164 (M$^+$).

EXAMPLE 3

Procedure for 1,2,5,6-tetrahydronicotinonitrile (12) Synthesis

An oven dried round bottom flask was charged with 3'-methoxy acetophenone (300 mg, 2 mmol, 1 equiv.), malononitrile (165 mg, 2.5 mmol, 1.5 equiv.) and QuFs (4) 438 mg or (5) 494 mg, 2 mmol, 1 equiv.) at room temperature. The resulting mixture was heated at 95-100° C. for 12-14 h until the complete consumption of starting material. The reaction mixture was cooled to room temperature and diluted with dioxane (5 mL). The dilute mixture was then added to 20% HCl aqueous solution to afford yellow precipitate of 1,2,5,6-tetrahydronicotinonitrile (12). The precipitates of (12) were further washed with 20% HCl solution for the complete removal of ionic salt. Precipitates were collected and dried for further spectroscopic analysis. $^1$H NMR showed >90% purity of 1,2,5,6-tetrahydronicotinonitrile derivative (12) (238 mg, 60%) (Table-3).

TABLE 3

NMR Data of 2-dicyanomethylene-6-methyl-4,6-bis(m-methoxyphenyl)-1,2,5,6-tetrahydronicotinonitrile (12).

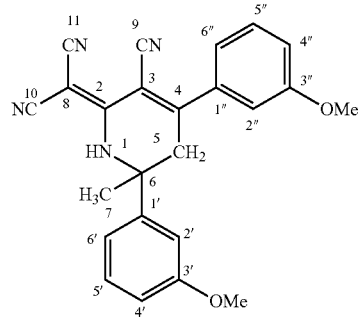

| Atom (N or C) # | $\delta_C$ | $\delta_H$ | Mul. | HBMC | COSY | NOESY |
|---|---|---|---|---|---|---|
| 1 | — | 9.71 | NH | C-2, C-3, C-5, C-6, C-7, C-8, C-10 | H$^a$-5, H-6' | H-2', H-7 |
| 1' | 144.6 | — | C | — | — | — |
| 1" | 136.8 | — | C | — | — | — |
| 2 | 157.5 | — | C | — | — | — |
| 2' | 111.5 | 6.98 (brs) | CH | C-3', C-6, C-6' | — | H-1, H$^a$-5, H-6', H-4', H-7, H-12 |
| 2" | 113.4 | 6.91 (brs) | CH | C-3", C-4, C-4", C-6" | — | H-6", H-4", H-13 |
| 3 | 101.2 | — | C | — | — | — |
| 3' | 159.5 | — | C | — | — | — |
| 3" | 159.1 | — | C | — | — | — |
| 4 | 168.6 | — | C | — | — | — |
| 4' | 112.5 | 6.88 (dd, J = 2.4, 10.4 Hz) | CH | C-2', C-6' | H-5', H-6' | H-5', H-6', H-12 |
| 4" | 117.6 | 7.14 (dd, J = 2.2, 9.2 Hz) | CH | C-2", C-6" | H-5", H-6" | H-5", H-6", H-13 |
| 5 | 43.8 | 3.77 (d, 18.4 Hz)* | CH$^a$H | C-1', C-1", C-3, C-4, C-6, C-7 | H$^b$-5 | H$^b$-5 |
|  |  | 3.27 (d, 18.4 Hz) | CHH$^b$ | C-1', C-1", C-2, C-2", C-3, C-4, C-6, C-7 | H$^a$-5 | H-2', H-2", H$^a$-5, H-6" |
| 5' | 129.8 | 7.33 (t, J = 8 Hz) | CH | C-1', C-3' | H-4', H-6' | H-4', H-6' |
| 5" | 130.1 | 7.43 (t, J = 8 Hz) | CH | C-1", C-3" | H-4", H-6" | H-4", H-6" |
| 6 | 56.9 | — | C | — | — | — |
| 6' | 117.1 | 6.95 (d, J = 8.4 Hz) | CH | C-2', C-4', C-6 | H-4', H-5' | H-2', H-4', H$^a$-5, H-5' |
| 6" | 120.4 | 7.03 (d, J = 7.6 Hz) | CH | C-2", C-4, C-4" | H-4", H-5" | H-2', H-4', H$^a$-5, H-5" |
| 7 | 28.2 | 1.71 (s) | CH$_3$ | C-1', C-5, C-6 | — | H-1, H-2', H$^a$-5 |
| 8 | 49.5 | — | C | — | — | — |
| 9 | 115.4 | — | CN | — | — | — |
| 10 | 113.6 | — | CN | — | — | — |
| 11 | 114.8 | — | CN | — | — | — |

TABLE 3-continued

NMR Data of 2-dicyanomethylene-6-methyl-4,6-bis(m-methoxyphenyl)-1,2,5,6-tetrahydronicotinonitrile (12).

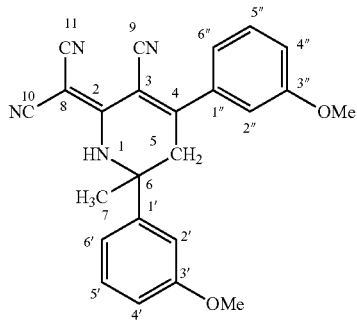 [SMILES: COc1cccc(C2=C(C#N)C(=C(C#N)C#N)NC(C)(c3cccc(OC)c3)C2)c1]

| Atom (N or C) # | $\delta_C$ | $\delta_H$ | Mul. | HBMC | COSY | NOESY |
|---|---|---|---|---|---|---|
| 12 | 55.1 | 3.75 (s) | OCH$_3$ | C-3' | — | H-2', H-4' |
| 13 | 55.3 | 3.77 (s) | OCH$_3$ | C-3'' | — | H-2'', H-4'', H-6'' |

*= Obscured by m-methoxy protons
Mul. = Multiplicity

EXAMPLE 4

Procedure for Pyrazole (15) Synthesis

An oven dried screw tight micro reaction vessel was charged with acetylacetonate (200 mg, 2 mmol, 1 equiv.), p-methoxy phenylhydrazine hydrochloride (383 mg, 2.2 mmol, 1.2 equiv.) and QuF (4) (438 mg, 2 mmol, 1 equiv.) at room temperature. The resulting reaction mixture was heated at 95-100° C. for 4 h until thin layered chromatography analysis showed no sign of starting material. The reaction mixture was cooled to room temperature and quenched with water. Crude material was extracted with EtOAc (15 mL×2) from aqueous phase. Combined organic layers (EtOAc) were dried over MgSO$_4$, filtered and evaporated in rotatory evaporator to afford crude mixture of (15). Silica gel column chromatography with eluents (EtOAc: Hexane, 2/8) was used to purify the compound (15) in 60% yield (242 mg). 3,5-Dimethyl-1-(p-methoxyphenyl)-1H-pyrazole spectral data; $^1$H NMR (300 MHz, DMSO): $\delta_H$ 7.33 (2H, d, J=8.7 Hz, ArH), 7.01 (2H, d, J=9 Hz, ArH), 5.99 (1H, CH), 3.78 (3H, ArOCH$_3$), 2.19 (CH$_3$), 2.13 (CH$_3$).

What is claimed is:
1. A method for the preparation of a fluoride salt of alkylated quinolone comprising:
   (a) alkylating quinolone with an alkyl halide having a carbon chain length between 2 and 7 in the presence of toluene by refluxing at 120-125C; and,
   (b) dissolving the product of step (a) in methanol, adding a saturated solution of potassium fluoride at room temperature, stirring overnight, evaporating methanol, adding dichloromethane to produce a mixture of an aqueous layer and an organic layer, separating the organic layer, drying the organic layer to yield a fluoride salt of an alkylated quinolone.
2. The method of claim 1, wherein the fluoride salt of alkylated quinolone is 1-ethylquinolin-1-ium fluoride, 1-pentylquinolin-1-ium fluoride or 1-heptylquinolin-1-ium fluoride.
3. The method of claim 2, wherein the fluoride salts of alkylated quinolone are thermally stable.

* * * * *